(12) United States Patent
Cech et al.

(10) Patent No.: US 7,946,706 B2
(45) Date of Patent: May 24, 2011

(54) LENS ASSEMBLY FOR VITREORETINAL SURGERY

(75) Inventors: Steven D. Cech, Aurora, OH (US);
Aaron V. Weber, Stow, OH (US)

(73) Assignee: Volk Optical Inc., Mentor, OH (US)

( * ) Notice: Subject to any disclaimer, the term of this patent is extended or adjusted under 35 U.S.C. 154(b) by 196 days.

(21) Appl. No.: 11/351,368

(22) Filed: Feb. 10, 2006

(65) Prior Publication Data

US 2007/0188699 A1    Aug. 16, 2007

(51) Int. Cl.
*G02C 7/02* (2006.01)
*A61F 2/14* (2006.01)

(52) U.S. Cl. ............... 351/160 R; 359/808; 359/811; 623/4.1

(58) Field of Classification Search ........... 359/642, 359/808, 811–830; 351/159–177, 218, 219; 623/4.1–6.64

See application file for complete search history.

(56) References Cited

U.S. PATENT DOCUMENTS

| 4,553,824 | A | * | 11/1985 | Abe ........................ 351/219 |
| 4,627,694 | A | | 12/1986 | Volk |
| 4,966,439 | A | * | 10/1990 | Althaus et al. ............. 359/820 |
| 5,523,810 | A | | 6/1996 | Volk |
| 5,793,524 | A | | 8/1998 | Luloh |
| 5,817,099 | A | | 10/1998 | Skolik et al. |
| 5,988,824 | A | | 11/1999 | Rowsey et al. |
| 6,558,316 | B2 | | 5/2003 | Kikuchi et al. |
| 6,695,775 | B2 | | 2/2004 | Watanabe et al. |
| 6,977,782 | B2 | * | 12/2005 | Maeda et al. ............... 359/819 |
| 7,338,170 | B2 | | 3/2008 | Cech et al. |
| 7,499,219 | B2 | | 3/2009 | Cech et al. |
| 2004/0085654 | A1 | * | 5/2004 | Okazaki ..................... 359/819 |

OTHER PUBLICATIONS

International Search Report.

* cited by examiner

*Primary Examiner* — Darryl J Collins
(74) *Attorney, Agent, or Firm* — Fay Sharpe LLP

(57) ABSTRACT

This invention is directed towards ophthalmic lenses used to assist during vitreoretinal surgery. More specifically, it is directed towards ophthalmic lenses that are constructed to generate a high-resolution image of the retinal surface during surgery while maintaining a minimal mechanical envelop all while using materials and assembly methods compatible with autoclave sterilization techniques.

13 Claims, 4 Drawing Sheets

LENS ASSEMBLY FOR VITREORETINAL SURGERY

BACKGROUND OF THE INVENTION

It is well known in the art to use suitably engineered diagnostic, therapeutic, and surgical ophthalmic lenses to provide an indirect image of the retina of a patient while under examination. By properly placing such a lens its designed working distance away from the corneal surface, an indirect image of the retinal surface is formed external to the eye structure. The indirect image of the curved retinal surface is typically formed in a generally flat image plane wherein it is available for convenient observation via one of many types of ophthalmic imaging devices that are known in the art—surgical stereomicroscopes and slit lamp stereomicroscopes being examples of such imaging devices.

U.S. Pat. No. 4,627,694 describes a lens that is designed to be used in conjunction with a slit lamp stereomicroscope to facilitate a diagnostic examination of a patient's retina during a standard office visit. This patent describes the use of a symmetrical double aspheric lens that, when positioned a prescribed distance away from the surface of the cornea, acts to form an indirect or aerial image of the patient's retina. This type of lens is often described as a non-contact ophthalmic lens in that it forms a high-resolution retinal image without requiring the lens to come into direct contact with the patient's eye.

Similarly, U.S. Pat. No. 5,523,810 describes the innovative attributes of one particular implementation of a contact style ophthalmic lens. In this particular implementation, the innovation primarily consists of using a compound contact lens element within the lens assembly. For the specific purpose of illustrating the innovation of the current invention, it is required to highlight that one of the surfaces of the lens assembly described in the U.S. Pat. No. 5,523,810 has been fabricated using a cornea-matching concave radius of curvature. This is done because this type of lens is designed to be placed in direct contact with the patient's eye during use. Another important attribute of the invention described in the U.S. Pat. No. 5,523,810 is the inclusion of a second imaging lens element spaced a distance away from the contact lens element. This second lens element is used in this implementation to collect and focus the light exiting the contact lens element and is primarily responsible for forming the aerial or indirect image of the retinal surface.

In U.S. Pat. No. 5,523,810, a housing is described which is used to securely mount the lens elements in place at a lens spacing that optimizes the image forming capability of the lens assembly. Typically the housing used in an ophthalmic lens assembly such as this takes the form of a contiguous 3-D conical surface manufactured out of an appropriate metal or polymer material. It is typical to affix the contact and imaging lens elements to the housing threaded inserts and epoxy and polymer O-ring sealants. The epoxy and O-ring sealants are used to form a liquid-tight internal spacing cavity between the two lens elements. Constructed in this fashion, the contact style imaging lens assembly of U.S. Pat. No. 5,523,810 is compatible with immersion in water or other appropriate liquid for the purpose of thorough cleaning between uses.

In addition to cleaning, it is essential to sterilize such a contact style ophthalmic lenses between uses to prevent the spread of infectious diseases. For lens assemblies as described in the U.S. Pat. No. 5,523,810 patent, the required sterilization step has historically been achieved using sterilizing gas such as ethylene oxide (ETO). However, it is widely known that there are undesirable attributes associated with ETO sterilization. First off, the per-item costs associated with ETO sterilization are relatively high. In addition, the turnaround time for an item that is sterilized using ETO is relatively long due to a mandatory aeration time that is required to remove the gas residuals that have adhered to the item after it exits the sterilization chamber.

Autoclave sterilization, or high-temperature steam sterilization is becoming the preferred method of sterilizing medical devices because of its inherently low costs, relatively quick turnaround time, and lack of any chemical disposal concerns. Autoclave sterilization is enacted by placing the item that is to be sterilized in a steam environment having a temperature between 120° and 135° and at an over pressure of 200,000 Kpa.

It has been shown that after exposing ophthalmic lenses constructed using epoxy and polymer O-ring sealants (as per U.S. Pat. No. 5,523,810) to a small number of autoclave cycles, water in both liquid and vapor forms begins to encroach into the sealed cavity between the contact and imaging lens elements. While sufficient for sealing out low pressure liquid water, the porosity of epoxies and polymer O-ring seals have been shown to be insufficient to prevent the encroachment of high-temperature/high-pressure steam, as found in an autoclave, into a sealed cavity between adjacent but spaced lens elements. Once water has breached into the internal cavity of a lens so constructed and has condensed onto the internal lens surfaces, those surfaces have to be cleaned and dried of any condensed moisture before the lens can be effectively applied again. Lenses of this type are not well suited for disassembly and cleaning, as they require special tools and disassembly/assembly procedures to facilitate completion of these actions.

U.S. patent application Ser. No. 11/251,112, filed Oct. 14, 2005, describes a multi-element ophthalmic imaging lens that is compatible with a steam autoclave. In this patent application, the concept of opening up the housing body so that there is no longer an internal spacing cavity to collect condensed moisture is introduced and implementation details presented. Constructed in the fashion outlined in the Ser. No. 11/251,112 application, both surfaces of the contact lens element as well as the imaging lens element are exposed to the sterilizing and subsequent drying cycles associated with a complete autoclave cycle. The possibility of moisture permanently encroaching into an internal cavity is therefore eliminated from concern.

While an implementation as described in application Ser. No. 11/251,112 does eliminate the need to effect an autoclave resistant seal on an internal spacing cavity and is therefore suitably autoclavable, an open-cavity design as described in this application does result in the undesirable feature of leaving the opposed contact lens and imaging lens surfaces exposed to the possibility of experiencing fluid splashes or condensation fogging during the course of surgery. The prospect of achieving a hermetically-sealed, autoclave-compatible internal spacing cavity is ideally prescribed for autoclavable ophthalmic imaging lenses.

U.S. Pat. No. 6,695,775 B2 describes a lens assembly for use within autoclavable endoscopes. To address the deficiencies associated with using epoxies or polymer O-rings as sealing agents within autoclavable lens assemblies, U.S. Pat. No. 6,695,775 B2 introduces the innovation of applying, by evaporative coating or by plating, a film of metal to the outside periphery of the physical lens element. Properly prepared in this fashion, metal solder can then be used to hermetically seal the prepared lens element to other properly prepared lens elements or, alternately, directly to a metal mounting structure. By using metal solder, an effective seal can be made that will allow a hermetically sealed internal spacing cavity to be maintained even after multiple exposures to autoclave sterilization.

Though the technology described in U.S. Pat. No. 6,695,775 B2 adequately allows a hermetically-sealed internal spacing cavity to be formed in lens assemblies that are required to be compatible with autoclave sterilization, the evaporative coating/plating processes as well as the laser-based metal soldering process which is required to effect proper sealing are highly specialized. These specialized manufacturing processes require the skilled operation of expensive manufacturing equipment. As a result, a more accessible means of creating an autoclave-compatible hermetic seal for ophthalmic lens assemblies still remains a goal.

SUMMARY OF THE INVENTION

In one aspect of the presently described embodiments, a lens assembly comprises a lens and a support element having the lens positioned therein, wherein the lens is bonded to the support element with solder glass.

In another aspect of the presently described embodiments, the support element is a housing.

In another aspect of the presently described embodiments, the lens is positioned within one end of the housing.

In another aspect of the presently described embodiments, a second lens is positioned within a second end of the housing.

In another aspect of the presently described embodiments, the second lens is bonded to the housing with solder glass.

In another aspect of the presently described embodiments, the lens, the housing and the second lens defines a hermetically sealed cavity.

In another aspect of the presently described embodiments, the lens is formed with one or more aspheric optical surfaces.

In another aspect of the presently described embodiments, the lens assembly is an ophthalmic lens assembly.

In another aspect of the presently described embodiments, the ophthalmic lens assembly is operative as a non-contact lens assembly for vitreoretinal surgery.

In another aspect of the presently described embodiments, the ophthalmic lens assembly is operative as a contact lens assembly for vitreoretinal surgery.

In another aspect of the presently described embodiments, the support element is a metal frame assembly.

In another aspect of the presently described embodiments, the metal frame assembly comprises a metal ring and a handle.

In another aspect of the presently described embodiments, the support element comprises a second lens.

In another aspect of the presently described embodiments, the lens assembly comprises a substantially cylindrical housing having a first open end and a second open end, a first lens positioned within the first end of the housing, the first lens bonded to the housing with glass solder and a second lens positioned with the second end of the housing, the second lens bonded to the housing with glass solder, wherein the housing, the first lens and the second lens define a hermetically sealed cavity.

In another aspect of the presently described embodiments, the first lens is formed with one or more aspheric optical surfaces.

In another aspect of the presently described embodiments, the second lens is formed with one or more aspheric optical surfaces.

In another aspect of the presently described embodiments, a method comprises providing a support element, positioning a lens within the support element, providing solder glass material between the lens and the support element, and selectively heating and cooling the assembly to facility bonding of the lens to the support element.

In another aspect of the presently described embodiments, the method further comprises positioning a second lens within the support element and glass soldering the second lens to the support element.

In another aspect of the presently described embodiments, the first lens, the housing and the second lens define a hermetically sealed housing.

DETAILED DESCRIPTION OF THE PREFERRED EMBODIMENT

Figure 1:
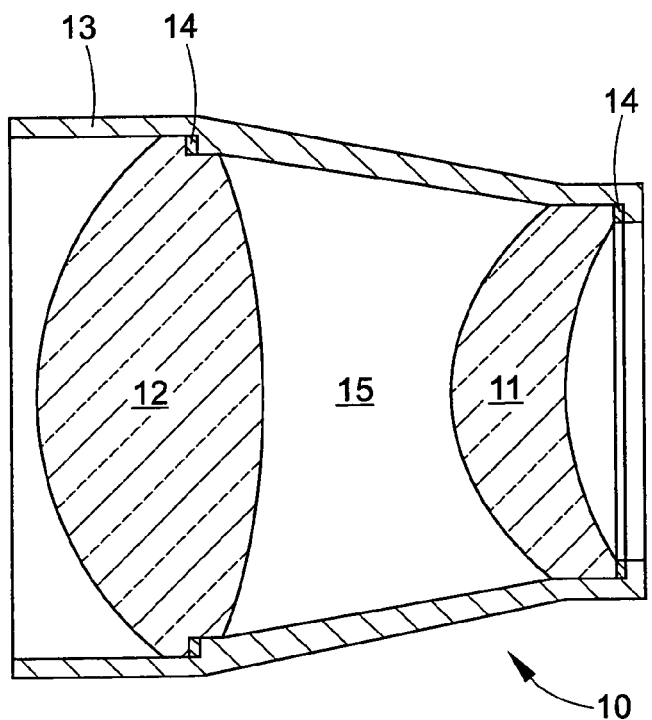
FIG. 1 shows a cross-sectional view of one embodiment of a sealed ophthalmic lens for vitreoretinal surgery according to the presently described embodiments.

One implementation of a lens assembly for vitreoretinal surgery 10 according to the presently described embodiments is shown in cross-section in FIG. 1. In FIG. 1, an imaging lens element 12 is spaced an advantageous distance from a contact lens element 11 using a support element or generally conical and contiguous housing 13 having opposed ends to establish and maintain the proper lens-to-lens spacing. In one form, both the contact lens element 11 and the imaging lens element 12 are fabricated out of optical glass material that is generally compatible with the environment of a steam autoclave.

Standard glass types that are primarily comprised of semi-metal compounds have been experimentally proven to deteriorate rapidly when exposed to the harsh environment of a steam autoclave. U.S. Pat. No. 6,558,316 B2 describes the results of experiments that show how compounds of semi-metals are prone to dissolving out of the polished lens substrate when it is exposed to the high temperature and pressure environment of a steam autoclave. Once out, the disassociate ions tend to react with the elements of the vapor to form impurities that attack and then imbed into the surface of the polished glass. These surface impurities accumulate over time and work to reduce the ability of the lens to transmit or focus light.

In general, the steps taken to increase the index-of-refraction of optical glasses (replace some of the semi-metal composition with other molecular compounds) tend to have the additional beneficial effect of making the glass more compatible with steam autoclave sterilization. However, experimentation using the custom glass compounds described in U.S. Pat. No. 6,558,316 B2 as well as other experimentation using commercially available glass compounds has indicated that not all high index-of-refraction glasses are equal in terms of autoclave compatibility. Through experimentation it has been shown that compounds of alkali metals (ex. BaO, CaO) and alkaline earth metals (ex. $K_2O$, $Na_2O$) tend to readily dissolve out of the solid glass and, when out, react quickly and efficiently to form deleterious impurity sites along the surface of the polished lens. In contrast, compounds of rare earth elements (ex. $La_2O_3$, $Gd_2O_3$) tend not to dissolve out under the conditions of a steam autoclave. This makes them much more stable and compatible with an autoclave. Furthermore, other compounds that are neither of the types that are described as rare earth metals, alkali metals, nor alkaline earth metals (examples of which are $Y_2O_3$ and $Ta_2O_5$) have properties that make them intermediate performers in regard to autoclave-compatibility.

Analysis and experimentation (more completely documented in U.S. patent application Ser. No. 11/251,112, filed Oct. 14, 2005, and entitled Lens System for Vitreoretinal Surgery and U.S. Provisional Patent Application Ser. No. 60/726,857, filed on Oct. 14, 2005, both of which are incorporated herein by reference in their entirety) has shown that glass material may be selected so that it has the following compositional properties which, in summation, should result in an image forming lens 10 generally compatible with the environment of the steam autoclave.

$SiO_2$% comp. weight+$B_2O_3$ comp. weight<50% total comp. weight

% comp. weight alkali metal compounds+% comp. weight alkaline earth metal compounds<10% total comp. weight.

($SiO_2$+$B_2O_3$% comp. weight)/(rare earth % comp. weight) <1

For further clarification of the preferred compositional content of autoclave compatible glasses, the compositional content of three different optical glass types are presented below.

| Compound | Hikari E-LASF08 MSDS Listed | Hikari E-LASF08 Used for analysis | Ohara N-LAH58 MSDS Listed | Ohara N-LAH58 Used for analysis | Hikari N-LAK8 MSDS Listed | Hikari E-LAK8 Used for analysis |
|---|---|---|---|---|---|---|
| $SiO_2$ | <10% | 4% | 3-8% | 4% | <10% | 4% |
| $B_2O_3$ | 10-20% | 10% | 5-15% | 10% | 30-40% | 35% |
| $La_2O_3$ | 40-50% | 40% | 25-35% | 30% | 40-50% | 45% |
| $Gd_2O_3$ | 10-20% | 20% | 25-35% | 30% | | |
| $Ta_2O_5$ | 10-20% | 15% | 15-25% | 20% | | |
| $Nb_2O_5$ | <10% | 2% | <2% | 1% | | |
| $ZrO_2$ | <10% | 4% | 3-8% | 4% | <10% | 4% |
| $Sb_2O_3$ | <1% | 0.25% | <0.5% | 0.25% | <1% | 0.25% |
| $SnO_2$ | | | <1% | 0.75% | | |
| BaO | <1% | 0.25% | | | <1% | 0.25% |
| $WO_3$ | <1% | 0.5% | | | | |
| $Yb_2O_3$ | <10% | 4% | | | | |
| CaO | | | | | <10% | 5% |
| $Y_2O_3$ | | | | | <1% | 0.5% |
| ZnO | | | | | <10% | 6% |
| | | 100% | | 100% | | 100% |

The columns identified as "MSDS Listed" represent the content of the glass as published by the manufacturer in their Material Safety Data Sheets (MSDS). The highlighted column identified as "Used for analysis" lists a reasonable compositional value that is used for the purposes of generating a best estimate of the actual composition of the indicted glass types.

The analysis that follows uses the compositional rules defined by this invention to predict a result that 2 of the glass types listed above (Hikari E_LASF08 and Ohara N-LAH58) should be superior performers in regard to autoclave compatibility. The same rules applied to the third glass type (Hikari E-LAK8) indicate that it will be a marginally acceptable solution in regard to autoclave compatibility.

| | Hikari E-LASF08 | Ohara N-LAH58 | Hikari E-LAK8 |
|---|---|---|---|
| $SiO_2$ + $B_2O_3$ comp. weights < 50% total | 4% + 10% = 14% (*10% + 20% = 30%*) | 4% + 10% = 14% (*8% + 15% = 23%*) | 4% + 35% = 39% (*10% + 40% = 50%*) |
| Akali metals + alkaline earth metal comp. weights < 10% total | BaO = 0.25% (*BaO = 1%*) | 0% | BaO + CaO 0.25% + 5% = 5.15% (*1% + 10% = 11%*) |
| ($SiO_2$ + B2O3 comp. weights)/(rare earth comp. weights) < 1 | 14%/($La_2O_3$ + $Gd_2O_3$ + $Yb_2O_3$) 14%/(40% + 20% + 4%) 14%/64% = 0.22 (*30%/50% = 0.6*) | 14%/($La_2O_3$ + $Gd_2O_3$) 14%/(30% + 30%) 14%/60% = 0.23 (*23%/50% = 0.46*) | 39%/($La_2O_3$) 39%/45% = 0.87 (*50%/40% = 1.25*) |

In the above analysis, the formulation rules governing the selection of a preferred glass type as defined by this invention are applied to the reasonable best estimate compositional values. Also supplied in italics are the worst-case values for the formulation metrics given the range of possible compositional values allowed by the published MSDS data.

Experimentation on the general compatibility of these three different high index-of-refraction glass types to the environment of the autoclave has confirmed agreement with the results predicted by tabulated analysis. More specifically, experiments have shown that the glass types E-LASF08 and N-LAH58 are superior glass types in regard to autoclave compatibility. Additionally, the glass type E-LAK8 has an acceptable (but not superior) autoclave compatibility rating.

It is typical in the art to use spherical optical surfaces in lenses to form images of objects of interest. It is also known in the art that the use of aspheric optical surfaces is preferred when high-resolution images of the surface of the retina are required to be formed. The use of aspheric surfaces minimizes the amount of image aberration inherent in the resulting retinal image. As such, the use of aspheric lens elements for both the imaging lens element 12 as well as the contact lens element 11 is the preferred implementation of the subject invention.

In one form, the support element or housing 13 of FIG. 1 is advantageously fabricated using a metal possessing a thermal expansion coefficient that is similar to the glass material used to fabricate the imaging 12 and contact 11 lens elements. Selected glass types having properties that are compatible with autoclave sterilization have thermal expansion coefficients in the range of $6-7\times10^{-6}$ mm/mm° C. Titanium and its alloys possess thermal expansion coefficients in the range of $8.5-9.5\times10^{-6}$ mm/mm° C. and have proven to be adequately matched to the expansion properties of preferred autoclave-compatible glass types. Based on this fact and its ease of manufacturability, titanium and its alloys have proven to be preferred materials from which to form the housing 13. The housing may take a variety of forms. Though titanium and its alloys are referenced here as exemplary materials for forming the housing 13 (as well as other housings and support elements described herein), other metal, glass, or ceramic materials possessing an appropriate thermal expansion coefficient and an ability to be machined into the required forms are understood to be applicable to the subject invention.

In FIG. 1, both the contact lens element 11 and the imaging lens element 12 are bonded and sealed to the support element or housing 13 using an appropriate solder glass 14. In one form, a solder glass 14 has a relatively low sealing temperature as well as a thermal expansion coefficient matched to the materials used to fabricate the contact 11 and imaging 12 lens elements as well as the support element or housing 13. There are a variety of commercially available solder glasses known in the art that possess the properties that allow them to be successfully used to seal glass lens elements to titanium.

Solder glass is known in the art to be supplied in at least two forms. In one form, it is provided as a powder of user specified particle size. In this form, the solder glass is typically mixed with an appropriate solvent to form a solution that would ultimately be delivered to the sealing/bonding site using syringes or other means that are typically used to apply epoxies or other adhesives.

In a second form, the solder glass is supplied in the form of thin, flexible tapes or performs. To create this more processed form of the product, solder glass in powdered form is mixed into a solution wherein a binding agent is added. This solution containing solvent, binding agent, and solder glass is extruded into long thin films. These films are left to harden (upon evaporation of the solvent) into a flexible tape or paper-like solid material. In this form, the solder glass tape can be cut or stamped into a variety of shapes to fit the needs of a particular application. For the ophthalmic lens outline in FIG. 1, one possible shape is a contiguous annulus shape similar to an O-ring. Configured as described, a suitable solder glass 14 could be supplied to the sealing area of the housing 13 in the form of two (2) O-ring solder glass preforms, one for the contact lens element 11 and one for the imaging lens element 12. The contact lens element 11 and the imaging lens element 12 could then be placed appropriately in the housing (in contact with the solder glass preform) in preparation for the sealing step.

To enact proper sealing between the lens elements 11/12 and the housing 13, the solder glass 14 is, in one form, taken to an elevated temperature above the sealing temperature of the solder glass. Solder glasses having sealing temperatures in the 400°-600° C. range are well known in the art. A solder glass having a sealing temperature in the 400°-500° C. range would be preferred for this application. Once the solder glass gets above its softening point temperature it starts to deform in shape. As heat continues to be applied and the temperature continues to raise, the solder glass gets to a point wherein it flows freely onto the opposed sealing surfaces of the contact/imaging lens elements 11/12 and the housing 13. A hermetic seal is formed as the solder glass 14 is taken through a subsequent cooling cycle.

For the sealing process to perform as described, the contact/imaging lens elements 11/12, as well as the housing 13, have transformation or melting temperatures well above the specified upper sealing temperature of the solder glass 14. Titanium and its alloys melt well above (1000°-1700° C. range) the 400°-500° C. upper sealing range of preferred solder glass types. Additionally, selected autoclave-compatible glass (from which are formed the contact lens element 11 as well as the imaging lens element 12) can be found that possess material transformation and softening point temperatures in the 700°-800° C. range. Thus, with a suitable selection of materials well known in the art, the implementation of an autoclave-compatible ophthalmic lens according to the specific principles outlined in this disclosure is possible.

Returning again to FIG. 1, upon cooling and sealing, a hermetically sealed internal spacing cavity 15 is formed in the ophthalmic lens assembly 10. The solder glass seal 14 will prevent water in the form of liquid or vapor from encroaching into the lens thus preventing deleterious damage from occurring.

Figure 2:
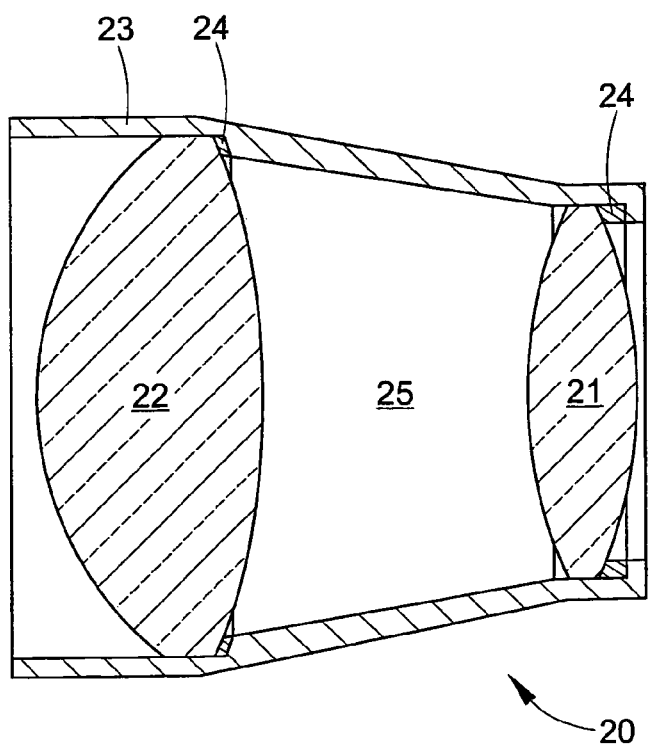
FIG. 2 shows a cross-sectional view of an alternate implementation of a sealed ophthalmic lens for vitreoretinal surgery according to the presently described embodiments wherein the cornea-contacting lens element is replaced with a biconvex lens element.

FIG. 2 shows a cross-sectional view of an alternative implementation of a sealed ophthalmic lens for vitreoretinal surgery 20. Instead of a contact lens element 11 as is illustrated in FIG. 1, the lens assembly 20 has a biconvex lens element 21 integrated into its design. In FIG. 2, both an imaging lens element 22 and a biconvex lens element 21 are appropriately sealed to a support element in the form of a housing 23 using solder glass 24. In doing so, a hermetically sealed internal spacing cavity 25 is adequately formed.

Figure 3:
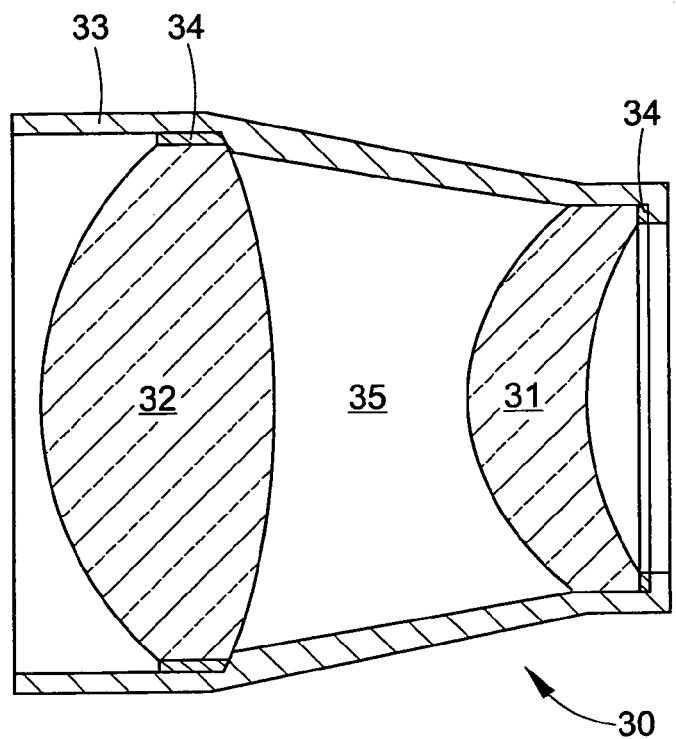
FIG. 3 shows a cross-sectional view of an alternate implementation of a sealed ophthalmic lens for vitreoretinal surgery according to the presently described embodiments wherein the imaging lens element is sealed about its outer edge.

FIG. 3 shows a cross-sectional view of an alternate implementation of a sealed ophthalmic lens for vitreoretinal surgery 30. In this implementation, solder glass 34 is used to seal a contact lens element 31 and a imaging lens element 32 to a support element taking the form of a housing 33. In this implementation, the imaging lens element 32 is sealed to the housing 33 about its outer edge. In doing so, a hermetically sealed internal spacing cavity 35 is adequately formed.

Figure 4:
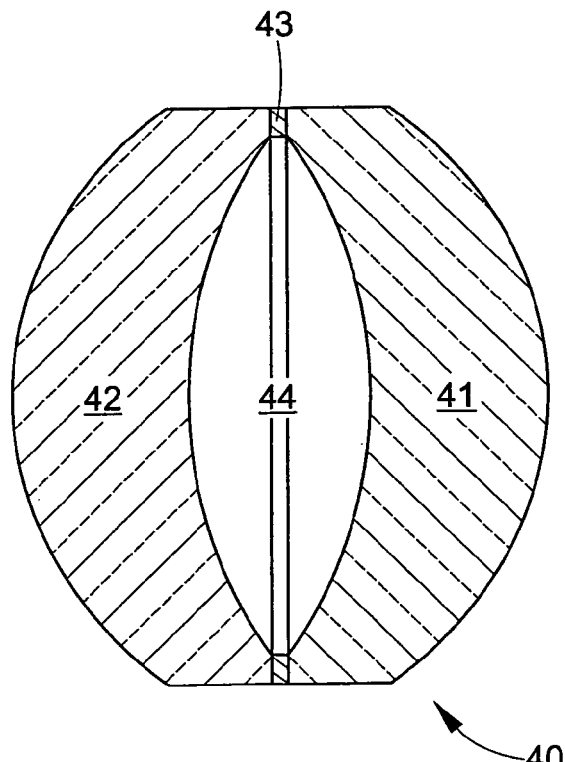
FIG. 4 shows a cross-sectional view of an alternate implementation of a sealed ophthalmic lens for vitreoretinal surgery according to the presently described embodiments wherein two individual lens elements are sealed directly to one another.

FIG. 4 shows a cross-sectional view of an alternate implementation of a sealed ophthalmic lens for vitreoretinal surgery 40. In this implementation, solder glass 43 is used to seal an imaging lens element 42 directly to a concave lens element 41. In doing so, a hermetically sealed internal spacing cavity 44 is adequately formed. In this form, the support element takes the form a second lens, either the imaging lens element 42 or the concave lens element 41.

Figure 5:
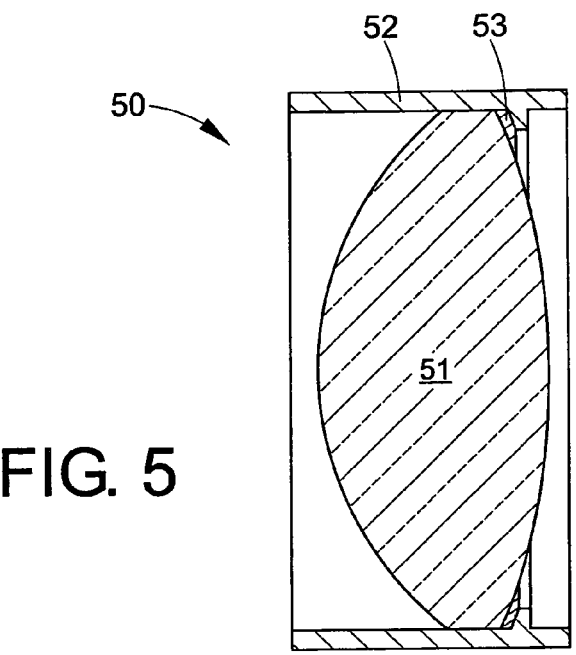
FIG. 5 shows a cross-sectional view of a non-contact ophthalmic lens for vitreoretinal surgery according to the presently described embodiments wherein the lens is bonded directly to a housing structure allowing the overall size of the lens assembly to be minimized while its clear aperture is maximized.

FIG. 5 shows a cross-sectional view of a non-contact ophthalmic lens for vitreoretinal surgery 50. In lens assembly 50, solder glass 53 is used to mechanically bond a lens element 51 directly to a support element such as a housing 52. In doing so, the requirement for a mechanical insert to affix the lens element 51 into the housing 52 is eliminated. A mechanical insert typically adds size to the overall assembly. Additionally, it tends to cover or otherwise block some of the polished lens surface of lens element 51 thus reducing its clear aperture or field-of-view (FOV). Both of these lens attributes, reduced FOV and increase physical size, negatively effects the perceived performance of ophthalmic lenses designed for vitreoretinal surgery.

Figure 6:
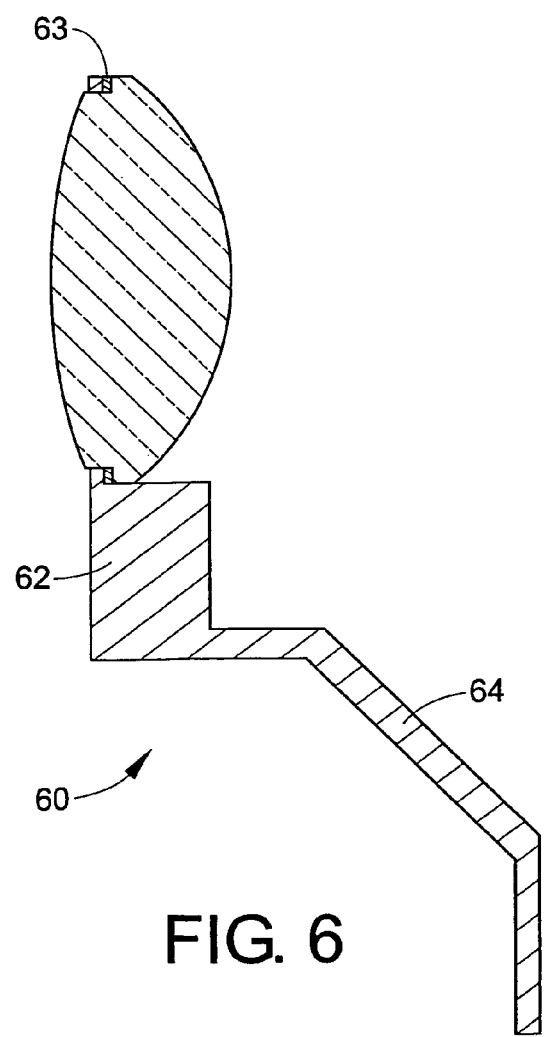
FIG. 6 shows a cross-sectional view of a non-contact ophthalmic lens for vitreoretinal surgery according to the presently described embodiments wherein the housing structure has an integrated handle to assist the supporting of the lens.

FIG. 6 shows a cross-sectional view of a non-contact ophthalmic lens for vitreoretinal surgery 60. In lens assembly 60, solder glass 63 is used to mechanically bond an imaging lens element 61 directly to a support element taking the form of a support ring/housing 62. A handle 64 is advantageously attached to the ring/housing 62 via standard mechanical means to assist the supporting of the lens.

Figure 7:
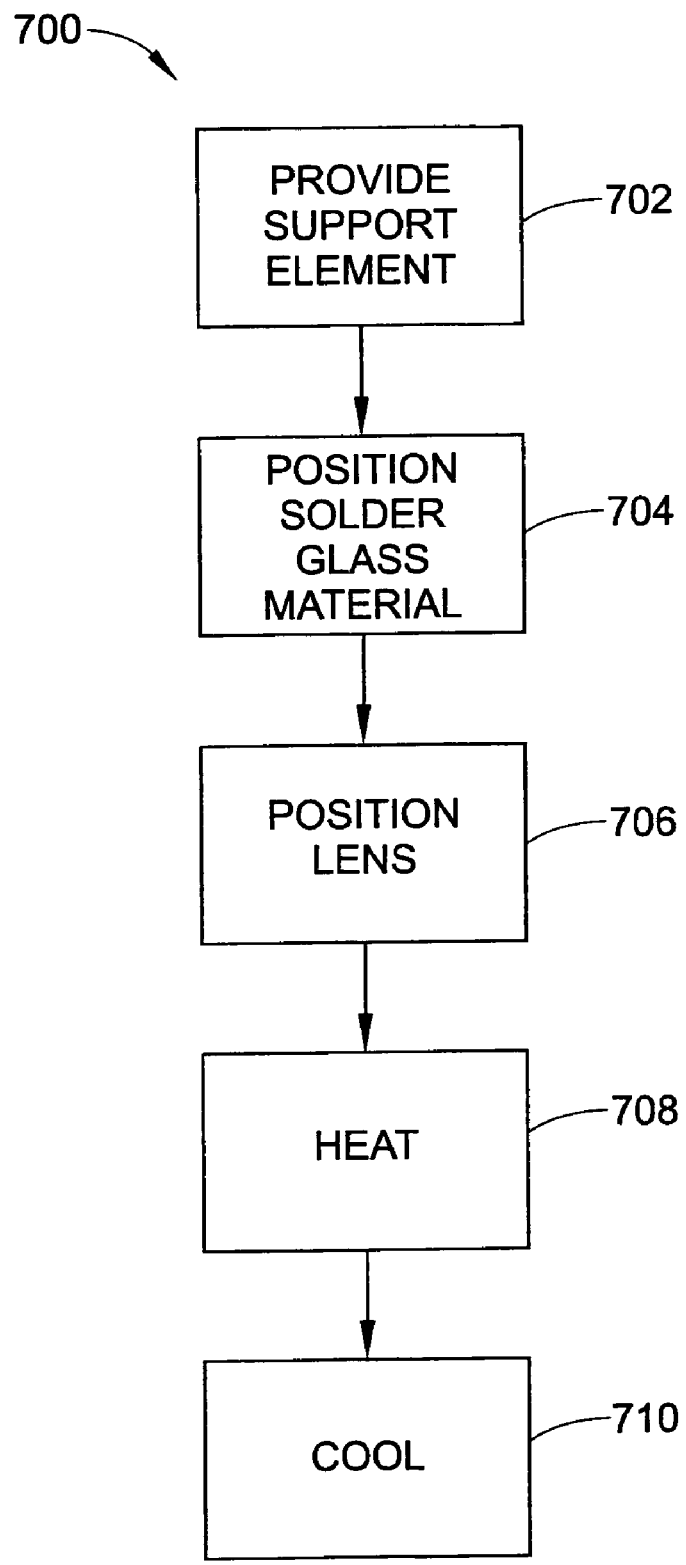
FIG. 7 is a flowchart illustrating a method according to the presently described embodiments

With reference to FIG. 7, a method according to the presently described embodiments is illustrated. As shown, a method 700 includes providing a support element (at 702). Of course, depending on the embodiment of the lens assembly contemplated, the providing of the support element may include the provision of a variety of different structures, e.g. housings, lenses, or metal rings. Next, suitable solder glass material is positioned at a bonding or sealing interface of the support element (at 704). As noted above, the solder glass material may take a variety of forms. Then, at least one lens is positioned within the support element such that a bonding or sealing surface of the lens is put in contact with the solder glass material precisely placed on the support (at 706). The positioning of the lens is a function of the support element and the overall lens assembly. For example, in some forms, two lenses are positioned within a housing, e.g., positioned within ends of the housing. In other forms, a single lens is positioned within a metal ring structure. The whole assembly is then heated to a temperature above the melting or sealing temperature of the solder glass material but below the melting deformation temperature of the lens and/or support element (at 708). The assembly is then cooled below the melting or sealing temperature of the solder glass material to facilitate bonding of the lens to the support element (at 710).

It should be appreciated that the implementation of the method may be accomplished in a variety of manners and combinations. For example, the solder glass material could be placed first on the lens, as opposed to the support element. In either case, the solder glass material is disposed between the lens and the support element.

Implementation of the presently described embodiments results in a variety of advantages. For example, an improved lens assembly for vitreoretinal surgery is provided that can withstand repeated cycles in an autoclave sterilizer without degrading in optical or mechanical performance. In addition, a sealed multi-element ophthalmic lens assembly is provided using glass solder to effect glass-to-glass or glass-to-metal bonding. The glass solder bonding for the contemplated structure minimizes its mechanical envelope and maximize its clear aperture.

We claim:
1. A lens assembly for vitreoretinal surgery comprising:
a first lens and a second lens; and,
a support element, formed of glass or ceramic material, having the first lens and the second lens positioned therein,
wherein the first lens and the second lens are bonded to the support element with solder glass.
2. The lens assembly as set forth in claim 1 wherein the support element is a housing.
3. The lens assembly as set forth in claim 2 wherein the first lens is positioned within one end of the housing.
4. The lens assembly as set forth in claim 3 wherein the second lens is positioned within a second end of the housing.
5. The lens assembly as set forth in claim 3 wherein the first lens, the housing and the second lens defines a hermetically sealed cavity.
6. The lens assembly as set forth in claim 1 wherein the lens is formed with one or more aspheric optical surfaces.
7. The lens assembly as set forth in claim 6 wherein the lens assembly is an ophthalmic lens assembly.
8. The lens assembly as set forth in claim 7 wherein the ophthalmic lens assembly is operative as a non-contact lens assembly for vitreoretinal surgery.
9. The lens assembly as set forth in claim 7 wherein the ophthalmic lens assembly is operative as a contact lens assembly for vitreoretinal surgery.
10. A lens assembly for vitreoretinal surgery comprising:
a lens; and,
a support element having the lens positioned therein,
wherein the lens is bonded to the support element with solder glass and wherein the support element comprises a metal ring and a handle.
11. An ophthalmic lens assembly useful in vitreoretinal surgery, the lens assembly comprising:
a substantially cylindrical housing having a first open end and a second open end;
a first lens positioned within the first end of the housing, the first lens bonded to the housing with glass solder; and,
a second lens positioned with the second end of the housing, the second lens bonded to the housing with glass solder,
wherein the housing, the first lens and the second lens define a hermetically sealed cavity.
12. The lens assembly as set forth in claim 11 wherein the first lens is formed with one or more aspheric optical surfaces.
13. The lens assembly as set forth in claim 11 wherein the second lens is formed with one or more aspheric optical surfaces.

* * * * *